United States Patent [19]

Moore, Jr.

[11] Patent Number: 4,659,823

[45] Date of Patent: Apr. 21, 1987

[54] HERBICIDAL COMPLEXES WITH UREAS

[75] Inventor: Earl P. Moore, Jr., Hockessin, Del.

[73] Assignee: E. I. Du Pont de Nemours & Company, Wilmington, Del.

[21] Appl. No.: 797,026

[22] Filed: Nov. 12, 1985

Related U.S. Application Data

[63] Continuation-in-part of Ser. No. 617,605, Jun. 5, 1984, abandoned.

[51] Int. Cl.$^4$ ............... C07C 251/42; C07C 251/46; C07C 239/42; C07C 239/47

[52] U.S. Cl. ..................... 544/212; 71/90; 71/92; 71/93; 544/211; 544/320; 544/321; 544/331; 544/332

[58] Field of Search ............. 544/320, 321, 331, 332, 544/211, 212; 71/90, 92, 93

[56] References Cited

U.S. PATENT DOCUMENTS 4,225,337  9/1980  Levitt ..................................... 71/90

Primary Examiner—Robert Gerstl

[57] ABSTRACT

Water-soluble complexes, which have herbicidal utility, can be formed from urea and alkali metal salts of selected sulfonylureas, e.g., chlorsulfuron.

9 Claims, No Drawings

HERBICIDAL COMPLEXES WITH UREAS

CROSS-REFERENCE TO RELATED APPLICATION

This application is a continuation-in-part of my co-pending application U.S. Ser. No. 617,605, filed June 5, 1984 abandoned.

BACKGROUND OF THE INVENTION

Sulfonylurea herbicides are well-known in the art. Such herbicides are often utilized in agriculturally suitable solvents. It is desirable to maximize the amount of sulfonylurea herbicide which can be dissolved in such a solvent so that one may make maximum use of the sulfonylurea herbicide.

Sulfonylurea herbicides are well-known in the art; there does not appear to be a teaching, however, to the formation of water-soluble complexes between urea, and urea derivatives with alkali metal salts of such sulfonylureas.

According to this invention it has unexpectedly been discovered that such complexes may be formed.

The complexes are more soluble in agriculturally suitable solvents which represents distinct advantages over the art; such as rapid formation of solutions for spraying, and higher concentrations of active ingredient in such solutions.

The comlexes also possess hydrolytic stability.

SUMMARY OF THE INVENTION

This invention pertains to products obtained by the process of contacting sulfonylurea salts of Formula I with ureas of Formula II under complexing conditions in a ratio of about 1:1, when m is 1, and about 1:2, when m is 2, to compositions containing said products and to their method-of-use as pre- and/or postemergence herbicides or plant growth regulants.

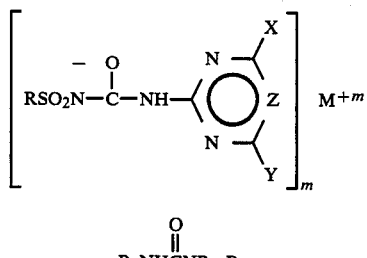

I

II wherein
R is

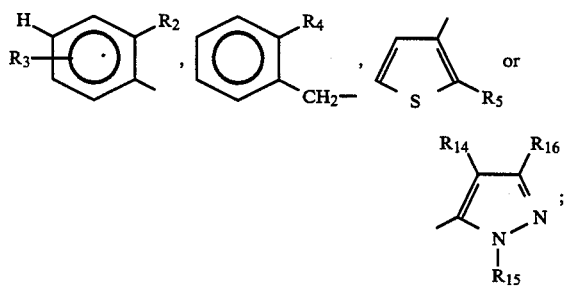

$R_1$ is H or CH$_3$;

$R_2$ is F, Cl, Br, $C_1$-$C_4$ alkyl optionally substituted with 1-3 atoms of F or Cl, $SO_2NR_6R_7$, $S(O)_nR_8$, $SO_2NCH_3(OCH_3)$, $CO_2R_9$, $OSO_2R_{10}$, $OR_{11}$, $NO_2$, $C_2$-$C_4$ alkenyl, $CONR_6R_7$, phenyl,

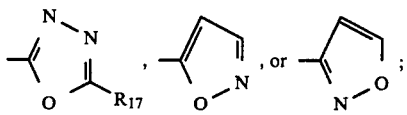

$R_3$ is H, F, Cl, Br, CH$_3$, OCH$_3$ or CF$_3$;
$R_4$ is Cl, NO$_2$, CO$_2R_{10}$;
$R_5$ is Cl, Br, $SO_2NR_6R_7$, $S(O)_nR_{10}$, $CO_2R_{10}$, $C_1$-$C_3$ alkyl, NO$_2$, CON(CH$_3$)$_2$ or $SO_2N(OCH_3)CH_3$;
$R_6$ is H or $C_1$-$C_3$ alkyl;
$R_7$ is H or $C_1$-$C_2$ alkyl;
$R_8$ is $C_1$-$C_3$ alkyl or $C_1$-$C_3$ alkyl substituted with 1-5 atoms of F, Cl or Br;
$R_9$ is $C_1$-$C_4$ alkyl, CH$_2$CH$_2$OCH$_3$, CH$_2$CH$_2$Cl or CH$_2$CH=CH$_2$;
$R_{10}$ is $C_1$-$C_3$ alkyl;
$R_{11}$ is $C_1$-$C_4$ alkyl, $C_1$-$C_3$ alkyl substituted with 1-5 atoms of F, Cl or Br, CH$_2$CH=CH$_2$ or CH$_2$C≡CH;
$R_{12}$ is H, $C_1$-$C_{12}$ alkyl, $C_3$-$C_6$ cycloalkyl or $C_3$-$C_6$ alkenyl;
$R_{13}$ is H, CH$_3$ or CH$_2$CH$_3$ or $R_{12}$ and $R_{13}$ may be taken together to be —(CH$_2$)$_4$— or —(CH$_2$)$_5$— or $R_1$ and $R_{12}$ may be taken together to be —(CH$_2$)$_2$—;
$R_{14}$ is $C_1$-$C_3$ alkyl, F, Cl, Br, NO$_2$, CO$_2R_{10}$, SO$_2$N(CH$_3$)$_2$, SO$_2R_{12}$, or phenyl;
$R_{15}$ is H, $C_1$-$C_3$ alkyl, or CH$_2$CH=CH$_2$;
$R_{16}$ is H or CH$_3$;
$R_{17}$ is H or CH$_3$;
n is 0 or 2;
M is an alkali metal cation, magnesium or calcium;
Z is CH or N;
X is CH$_3$, OCH$_3$ or OCHF$_2$;
Y is CH$_3$, OCH$_3$, CH(OCH$_3$)$_2$, OCHF$_2$, C$_2$H$_5$, OC$_2$H$_5$, OCH$_2$CF$_3$ or CH$_2$OCH$_3$; and
m is 1 or 2.

Preferred for reasons of their expected higher herbicidal activity and/or more favorable ease of synthesis and/or improved stability of compositions containing them are:

(1) complexes of the generic scope containing sulfonylurea salts of Formula I
wherein
R is

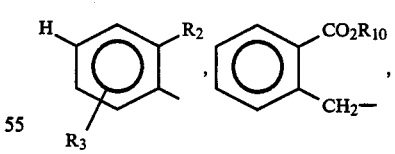

$R_2$ is Cl, CH$_3$, SO$_2$N(CH$_3$)$_2$, S(O)$_n$R$_8$, CO$_2$R$_9$, OSO$_2$R$_{10}$, OR$_{11}$, NO$_2$ or CON(CH$_3$)$_2$;
$R_3$ is H, Cl, CH$_3$, OCH$_3$ or CF$_3$;
$R_8$ is $C_1$-$C_3$ alkyl, CF$_3$, CF$_2$H or CF$_2$CF$_2$H;
$R_9$ is $C_1$-$C_4$ alkyl; and $R_{11}$ is $C_1$–$C_4$ alkyl, $CF_3$, $CF_2H$, $CF_2CF_2H$ or $CH_2CH_2Cl$;

(2) complexes of the generic scope containing the urea of Formula II wherein $R_1$, $R_{12}$ and $R_{13}$ are H;

(3) complexes of the preferred 1 where the sulfonylurea salt of Formula I is selected from the salts of:
2-[[(4-methoxy-6-methyl-1,3,5-triazin-2-yl)aminocarbonyl]aminosulfonyl]benzoic acid, methyl ester;
2-[(4,6-dimethylpyrimidin-2-yl)aminocarbonyl]aminosulfonyl]benzoic acid, methyl ester;
2-chloro-N-[(4-methoxy-6-methyl-1,3,5-triazin-2-yl)aminocarbonyl]benzenesulfonamide;
2-[[(4,6-dimethoxypyrimidin-2-yl)aminocarbonyl]aminosulfonylmethyl]benzoic acid, methyl ester;
5-[[(4,6-dimethoxypyrimidin-2-yl)aminocarbonyl]aminosulfonyl]-1-methyl-1H-pyrazole-4-carboxylic acid ethyl ester;
2-(2-Chloroethoxy)-N-[(4-methoxy-6-methyl-1,3,5-triazin-2-yl)aminocarbonylbenzenesulfonamide; and
3-[[(4-methoxy-6-methyl-1,3,5-triazin-2-yl)aminocarbonyl]aminosulfonyl]-2-thiophene-carboxylic acid, methyl ester.

(4) complexes of the preferred 3 containing the urea of Formula II where $R_1$, $R_{12}$ and $R_{13}$ are H;

(5) products of the generic process prepared from sulfonylurea salts of Formula I wherein R is

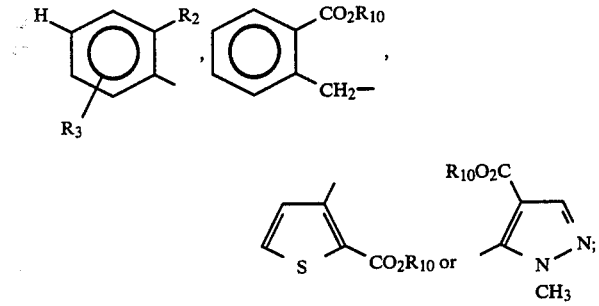

$R_2$ is Cl, $CH_3$, $SO_2N(CH_3)_2$, $S(O)_nR_8$, $CO_2R_9$, $OSO_2R_{10}$, $OR_{11}$, $NO_2$ or $CON(CH_3)_2$;
$R_3$ is H, Cl, $CH_3$, $OCH_3$ or $CF_3$;
$R_8$ is $C_1$–$C_3$ alkyl, $CF_3$, $CF_2H$ or $CF_2CF_2H$;
$R_9$ is $C_1$–$C_4$ alkyl; and
$R_{11}$ is $C_1$–$C_4$ alkyl, $CF_3$, $CF_2H$, $CF_2CF_2H$ or $CH_2CH_2Cl$;

(6) products of the generic process prepared from ureas of Formula II wherein
$R_1$ is H;
$R_{12}$ is $C_2$–$C_6$ alkyl; and
$R_{13}$ is H; and (7) products of the preferred 5 where the sulfonylurea salt is selected from the salts of:
2-[[(4-methoxy-6-methyl-1,3,5-triazin-2-yl)aminocarbonyl]aminosulfonyl]benzoic acid, methyl ester;
2-[(4,6-dimethylpyrimidin-2-yl)aminocarbonyl]aminosulfonyl]benzoic acid, methyl ester;
2-chloro-N-[(4-methoxy-6-methyl-1,3,5-triazin-2-yl)aminocarbonyl]benzenesulfonamide;
2-[[(4,6-dimethoxypyrimidin-2-yl)aminocarbonyl]aminosulfonylmethyl]benzoic acid, methyl ester;
5-[[(4,6-dimethoxypyrimidin-2-yl)aminocarbonyl]aminosulfonyl]-1-methyl-1H-pyrazole-4-carboxylic acid, ethyl ester;
2-(2-chloroethoxy)-N-[(4-methoxy-6-methyl-1,3,5-triazin-2-yl)aminocarbonyl]benzenesulfonamide; and
3-[[(4-methoxy-6-methyl-1,3,5-triazin-2-yl)aminocarbonyl]aminosulfonyl]-2-thiophenecarboxylic acid, methyl ester.

DETAILED DESCRIPTION OF THE INVENTION

This invention relates to novel reaction products of sulfonylurea salts of Formula I with ureas of Formula II, to the process for preparing them, to compositions containing them and to their method-of-use as pre- and postemergence herbicides or plant growth regulants. Agriculturally suitable salts of Formula I are also useful herbicides and can be prepared by a number of ways known to the art. For example, a metal salt of Formula I can be made by contacting the corresponding conjugate acid with a solution of an alkali or alkaline earth metal salt having an anion sufficiently basic to neutralize at least 95% of the conjugate acid (e.g., hydroxides, alkoxide, carbonate or hydroxide).

Salts of Formula I can also be prepared by exchange of one cation for another. Cationic exchange can be effected by direct reaction of a solution of a salt of Formula I with a solution containing the cation to be exchanged. This method is most effective when the desired salt containing the exchange cation has acceptably low solubility in the solvent and can be separated by filtration.

Exchange may also be effected by passing an aqueous solution of a salt of Formula I through a column packed with a cation exchange resin containing the cation to be exchanged. In this method, the cation of the resin is exchanged for that of the original salt and the desired product is eluted from the column.

The ureas of Formula II can be prepared by a number of ways well-known in the art. The simplest compound, urea, is commercially produced by reacting carbon dioxide and ammonia. Substituted ureas can be prepared by reacting primary or secondary amines with potassium cyanate or with urea in a water-free acid such as glacial acetic acid. Also, alkyl isocyanates or carbamoyl chlorides may be reacted with ammonia to give substituted ureas of Formula II. Additionally, substituted ureas useful in this invention can be made by reacting primary and secondary amines with esters of carbamic acid such as methyl or ethyl carbamate.

The products of this invention formed by reacting the sulfonylurea salts of Formula I where m is 1 or Formula I where m is 2 with ureas of Formula II where $R_1$ is hydrogen or methyl and $R_{12}$ and $R_{13}$ are hydrogen have been found to be 1:1 and 1:2 molar complexes respectively. That is, when a salt of Formula I where m is 1 and a urea of Formula II where $R_1$ is hydrogen or methyl and $R_{12}$ and $R_{13}$ are hydrogen are mixed in any molar proportion in a suitable solvent, the product which forms and is isolated contains an equimolar amount of each reactant. When a salt of Formula I, where m is 2 and a urea of Formula II where $R_1$ is hydrogen or methyl and $R_{12}$ and $R_{13}$ are hydrogen are mixed in any molar proportions in a suitable solvent, the product which forms and is isolated contains a 1:2 molar amount of the sulfonylurea and urea reactants. Solvents suitable for the preparation of complexes are any that will dissolve a sufficient amount of a sulfonylurea salt and urea compound to enable complete reaction to occur within an acceptable period of time, e.g., 5 minutes to 2 hours. These include water, alcohols such as methanol, ethanol and 2-propanol, ketones such as acetone, methyl isobutyl ketone, and methyl ethyl ketone, acetonitrile, tetrahydrofuran, γ-butyrolactone and N-methylpyrrolidone. In order to readily isolate a complex, the solvent preferably is one in which it has low solubility. For example, sodium salts of a number of sulfonylureas and urea are appreciably soluble in methanol but complexes formed are not. Alternatively, if solutions of complexes are desired, a good solvent for the complex is required. Complexes of lithium salts of most sulfonylureas and methylurea are fairly soluble in γ-butyrolactone, for example.

In general, lithium salts contribute more to complex solubility in any solvent than sodium salts and methylurea gives much improved solubility over urea.

Techniques for preparing complexes are relatively simple. A preformed metal salt of a sulfonylurea of Formula I prepared as described above may be mixed with a urea compound in a solvent or a sulfonylurea and equivalent amounts of a basic alkali or alkaline earth metal salt and a urea compound may be combined in any order in a solvent. Reaction to produce complexes is rapid, generally occurring to completion within 1–15 minutes.

Products of this invention formed by reacting the sulfonylurea salts of Formula I where m=1 with the ureas of Formula II where at least one of $R_1$, $R_{12}$ and $R_{13}$ is other than hydrogen or methyl or two of $R_1$, $R_{12}$ and $R_{13}$ are other than hydrogen also are complexes but exhibit somewhat different behavior than those prepared using the ureas of Formula II where $R_1$ is hydrogen or methyl and $R_{12}$ and $R_{13}$ are hydrogen. Complexes prepared from sulfonylurea salts of Formula I where m is 1 and the more highly substituted and/or higher alkyl substituted ureas under the complexing conditions described above in a ratio of about 1:1 have exceptionally high solubility in a variety of solvents and are not isolatable. Lithium salts contribute more to solubility than sodium salts, longer straight chain alkyl groups on ureas contribute more than substituents which are branched and solubility increases with chain length. Attempts to isolate complexes may result in complex dissociation.

Complex formation between sulfonylurea salts of Formula I where m is 1 and ureas of Formula II where at least one of $R_1$, $R_{12}$ and $R_{13}$ is other than hydrogen or methyl or two of $R_1$, $R_{12}$ and $R_{13}$ are other than hydrogen is shown by the fact that sulfonylurea salts which are virtually insoluble in a solvent are rapidly solubilized upon addition of the urea in an equal or greater molar proportion. For example, sodium salts of many sulfonylureas are slightly soluble in acetone but, when combined with n-butylurea, dissolve to an extent greater than 50%.

Products of this invention formed by reacting the sulfonylurea salts of Formula I where m is 2 with the ureas of Formula II where one of $R_1$, $R_{12}$ and $R_{13}$ is other than hydrogen or methyl or two of $R_1$, $R_{12}$ and $R_{13}$ are other than hydrogen afford 1:2 complexes which like the complexes with ureas of Formula II where $R_1$ is hydrogen or methyl and $R_{12}$ and $R_{13}$ are hydrogen are isolatable.

The products of this invention have been shown to have herbicidal activity equivalent to that of precursor sulfonylurea salts of Formula I as well as their corresponding conjugate acids. They may be formulated into a number of agriculturally acceptable forms such as solutions, oil suspensions, aqueous suspensions, wettable powders and granules.

The complexes are desirable products for agricultural usage because they are readily soluble in water and can be rapidly dissolved in preparing solutions for spraying.

Solutions of complexes from selected sulfonylurea salts and ureas in agriculturally suitable organic solvents can be prepared in higher concentrations than those of the sulfonylurea salts themselves and their corresponding conjugate acids. Stability of the sulfonylureas in these complexes in organic solvents is significantly improved compared to that of the same sulfonylureas as salts or conjugate acids in the same solvents. This enables formulations of solutions relatively stable in storage to be prepared.

The formulations of this invention may contain about 1 to 50%, (preferably 10 to 40%) of the complexes of sulfonylurea salts of Formula I and ureas of Formula II. Compositions may contain more than one complex. Compositions may also optionally contain other herbicides. The following herbicides are examples of materials which may be particularly useful in such combinations:

| Common Name | Chemical Name |
| --- | --- |
| acifluorfen | 5-[2-chloro-4-(trifluoromethyl)-phenoxy]-2-nitrobenzoic acid |
| alachlor | 2-chloro-2',6'-diethyl-N—(methoxymethyl)acetanilide |
| ametryn | 2-(ethylamino)-4-(isopropylamino)-6-methylthio)-s-triazine |
| amitrole | 3-amino-s-triazole |
| AMS | ammonium sulfamate |
| asulam | methyl sulfanilylcarbamate |
| atrazine | 2-chloro-4-(ethylamino)-6-(isopropylamino)-s-triazine |
| barban | 4-chloro-2-butynyl m-chlorocarbanilate |
| benefin | N—butyl-N—ethyl-α,α,α-trifluoro-2,6-dinitro-p-toluidine |
| bensulide | O,O—diisopropyl phosphorodithioate, S—ester with N—(2-mercaptoethyl)-benezenesulfonamide |
| benzipram | 3,5-dimethyl-N—(1-methylethyl)-N—(phenylmethyl)benzamide |
| benzoylprop | Ethyl N—benzoyl-N—(3,4-dichlorophenoxy)-DL-alaninate |
| bifenox | methyl 5-(2,4-dichlorophenoxy)-2-nitrobenzoate |
| bromacil | 5-bromo-3-sec-butyl-6-methyluracil |
| bromoxynil | 3,5-dibromo-4-hydroxybenzonitrile |
| butachlor | N—(butoxymethyl)-2-chloro-2',6'-diethylacetanilide |
| butam | 2,2-dimethyl-N—(1-methylethyl)-N—phenylmethyl)propanamide |
| buthidazole | 3-[5-(1,1-dimethylethyl)-1,3,4-thiadiazol-2-yl]-4-hydroxy-1-methyl-2-imidazolidinone |
| butralin | 4-(1,1-dimethylethyl)-N—(1-methylpropyl)-2,6-dinitrobenzenamine |
| cacodylic acid | hydroxydimethylarsine oxide |
| carbetamide | D-N—ethyllactamide carbanilate (ester) |
| CDAA | N,N—diallyl-2-chloroacetamide |
| CDEC | 2-chloroallyl diethyldithiocarbamate |
| chloramben | 3-amino-2,5-dichlorobenzoic acid |
| chlorbromuron | 3-(4-bromo-3-chlorophenyl)-1-methoxy-1-methylurea |
| chloroxuron | 3-[p-(p-chlorophenoxy)phenyl]-1,1-dimethylurea |
| chlorpropham | isopropyl m-chlorocarbanilate |
| cisanilide | cis-2,5-dimethyl-N—phenyl-1-pyrrolidinecarboxamide |
| CMA | calcium methanearsonate |
| cyanazine | 2-[[4-chloro-6-(ethylamino)-s-triazin-2-yl]amino]-2-methylpropionitrile |
| cycloate | S—ethyl N—ethylthiocyclohexanecarbamate |
| cycluron | 3-cyclooctyl-1,1-dimethylurea |
| cyperquat | 1-methyl-4-phenylpyridinium |
| cyprazine | 2-chloro-4-(cyclopropylamino)-6-(isopropylamino)-s-triazine |

| Common Name | Chemical Name |
|---|---|
| cyprazole | N—[5-(2-chloro-1,1-dimethylethyl)-1,3,4-thiadiazol-2-yl]cyclopropanecarboxamide |
| cypromid | 3',4'-dichlorocyclopropanecarboxanilide |
| dalapon | 2,2-dichloropropionic acid |
| dazomet | tetrahydro-3,5-dimethyl-2H—1,3,5-thiadiazine-2-thione |
| DCPA | dimethyl tetrachloroterephthalate |
| desmetryn | 2-(isopropylamino)-4-(methylamino)-6-methylthio)-s-triazine |
| diallate | S—(2,3-dichloroallyl)diisopropylthiocarbamate |
| dicamba | 3,6-dichloro-o-anisic acid |
| dichlobenil | 2,6-dichlorobenzonitrile |
| dichlorprop | 2-(2,4-dichlorophenoxy)propionic acid |
| diclofop | 2-[4-(2,4-dichlorophenoxy)phenoxy]propanoic acid |
| diethatyl | N—(chloroacetyl)-N—(2,6-diethylphenyl)glycine |
| difenzoquat | 1,2-dimethyl-3,5-diphenyl-1H—pyrazolium |
| dinitramine | $N^4,N^4$—diethyl-$\alpha,\alpha,\alpha$-trifluoro-3,5-dinitrotoluene-2,4-diamine |
| dinoseb | 2-sec-butyl-4,6-dinitrophenol |
| diphenamid | N,N—dimethyl-2,2-diphenylacetamide |
| dipropetryn | 2-(ethylthio)-4,6-bis(isopropylamino)-s-triazine |
| diquat | 6,7-dihydrodipyrido[1,2-a:2',1'-c]-pyrazinediium ion |
| diuron | 3-(3,4-dichlorophenyl)-1,1-dimethylurea |
| DSMA | disodium methanearsonate |
| endothall | 7-oxabicyclo[2.2.1]heptane-2,3-dicarboxylic acid |
| erbon | 2-(2,4,5-trichlorophenoxy)ethyl 2,2-dichloropropionate |
| ethafluralin | N—ethyl-N—(2-methyl-2-propenyl)-2,6-dinitro-4-(trifluoromethyl)benzenamine |
| ethofumesate | (±)-2-ethoxy-2,3-dihydro-3,3-dimethyl-5-benzofuranyl methanesulfonate |
| fenac | (2,3,6-trichlorophenyl)acetic acid |
| fenuron | 1,1-dimethyl-3-phenylurea |
| fenuron TCA | 1,1-dimethyl-3-phenylurea mono(trichloroacetate) |
| flamprop | N—benzoyl-N—(3-chloro-4-fluorophenyl)-DL-alanine |
| fluchloralin | N—(2-chloroethyl)-2,6-dinitro-N—propyl-4-(trifluoromethyl)aniline |
| fluometuron | 1,1-dimethyl-3-($\alpha,\alpha,\alpha$-trifluoro-m-tolyl)urea |
| fluorodifen | p-nitrophenyl $\alpha,\alpha,\alpha$-trifluoro-2-nitro-p-tolyl ether |
| fluridone | 1-methyl-3-phenyl-5-[3-(trifluoromethyl)phenyl]-4(1H)—pyridinone |
| fosamine | ethyl hydrogen (aminocarbonyl)phosphonate |
| glyphosate | N—(phosphonomethyl)glycine and agriculturally suitable salts thereof |
| hexaflurate | potassium hexafluoroarsenate |
| hexazinone | 3-cyclohexyl-6-(dimethylamino)-1-methyl-1,3,5-triazin-2,5(1H,3H)—dione |
| ioxynil | 4-hydroxy-3,5-diiodobenzonitrile |
| isopropalin | 2,6-dinitro-N,N—dipropylcumidine |
| karbutilate | tert-butylcarbamic acid ester with 3-(m-hydroxyphenyl)-1,1-dimethylurea |
| lenacil | 3-cyclohexyl-6,7-dihydro-1H—cyclopentapyrimidine-2,4(3H,5H)—dione |
| linuron | 3-(3,4-dichlorophenyl)-1-methoxy-1-methylurea |
| MAA | methanearsonic acid |
| MAMA | monoammonium methanearsonate |
| MCPA | [(4-chloro-o-tolyl)oxy]acetic acid |
| MCPB | 4-[(4-chloro-o-tolyl)oxy]butyric acid |
| mecoprop | 2-[(4-chloro-o-tolyl)oxy]propioninc acid |
| mefluidide | N—[2,4-dimethyl-5-[[(trifluoromethyl)sulfonyl]amino]phenyl]-acetamide |
| methalpropalin | N—(2-methyl-2-propenyl)-2,6-dinitro-N—propyl-4-(trifluoromethyl)benzenamide |
| metham | sodium methyldithiocarbamate |
| methazole | 2-(3,4-dichlorophenyl)-4-methyl-1,2,4-oxadiazolidine-3,5-dione |
| metoachlor | 2-chloro-N—(2-ethyl-6-methylphenyl)-N—(2-methoxy-1-methylethyl)acetamide |
| metribuzin | 4-amino-6-tert-butyl-3-(methylthio)-as-triazin-5(4H)one |
| molinate | S—ethyl hexahydro-1H—azepine-1-carbothioate |
| monolinuron | 3-(p-chlorophenyl)-1-methoxy-1-methylurea |
| monuron | 3-(p-chlorophenyl)-1,1-dimethylurea |
| monuron TCA | 3-(p-chlorophenyl)-1,1-dimethylurea mono(trichloroacetate) |
| MSMA | monosodium methanearsonate |
| napropamide | 2-($\alpha$-naphthoxy)-N,N—diethylpropionamide |
| naptalam | N—1-naphthylphthalamic acid |
| neburon | 1-butyl-3-(3,4-dichlorophenyl)-1-methylurea |
| nitralin | 4-(methylsulfonyl)-2,6-dinitro-N,N—dipropylaniline |
| nitrofen | 2,4-dichlorophenyl p-nitrophenyl ether |
| nitrofluorfen | 2-chloro-1-(4-nitrophenoxy)-4-(trifluoromethyl)benzene |
| norea | 3-(hexahydro-4,7-methanoindan-5-yl)-1,1-dimethylurea |
| norflurazon | 4-chloro-5-(methylamino)-2-($\alpha,\alpha,\alpha$-trifluoro-m-tolyl)-3(2H)—pyridazinone |
| oryzalin | 3,5-dinitro-$N^4,N^4$—dipropylsulfanilamide |
| oxadiazon | 2-tert-butyl-4-(2,4-dichloro-5-isopropoxyphenyl)$\Delta^2$-1,3,4-oxadiazolin-5-one |
| oxyfluorfen | 2-chloro-1-(3-ethoxy-4-nitrophenoxy)-4-(trifluoromethyl)benzene |
| paraquat | 1,1'-dimethyl-4,4'-bipyridinium ion |
| PBA | chlorinated benzoic acid |
| pendimethalin | N—(1-ethylpropyl)-3,4-dimethyl-2,6-dinitrobenzenamine |
| perfluidone | 1,1,1-trifluoro-N—[2-methyl-4-(phenylsulfonyl)phenyl]methanesulfonamide |
| picloram | 4-amino-3,5,6-trichloropicolinic acid |
| procyazine | 2-[[4-chloro-6-(cyclopropylamino)-1,3,5-triazine-2-yl]amino]-2-methylpropanenitrile |
| profluralin | N—(cyclopropylmethyl)-$\alpha,\alpha,\alpha$-trifluoro-2,6-dinitro-N—propyl-p-toluidine |
| prometon | 2,4-bis(isopropylamino)-6-methoxy-s-triazine |
| prometryn | 2,4-bis(isopropylamino)-6-(methylthio)-s-triazine |
| pronamide | 3,5-dichloro(N—1,1-dimethyl-2-propynyl)benzamide |
| propachlor | 2-chloro-N—isopropylacetanilide |
| propanil | 3',4'-dichloropropionalide |
| propazine | 2-chloro-4,6-bis(isopropylamino)-s-triazine |
| propham | isopropyl carbanilate |
| prosulfalin | N—[[4-(dipropylamino)-3,5-dinitrophenyl]sulfonyl]-S,S—dimethylsulfilimine |
| prynachlor | 2-chloro-N—(1-methyl-2-propynyl)-acetanilide |
| secbumeton | N—ethyl-6-methoxy-N'—(1-methylpropyl)-1,3,5-triazine-2,4-diamine |
| siduron | 1-(2-methylcyclohexyl)-3-phenylurea |
| simazine | 2-chloro-4,6-bis(ethylamino)-s-triazine |
| simetryn | 2,4-bis(ethylamino)-6-(methylthio)-s-triazine |
| TCA | trichloroacetic acid and its salts |
| tebuthiuron | N—[5-(1,1-dimethylethyl)-1,3,4-thiadiazol-2-yl]-N,N'—dimethylurea |
| terbacil | 3-tert-butyl-5-chloro-6-methyluracil |
| terbuchlor | N—(butoxymethyl)-2-chloro-N—[2-(1,1-dimethylethyl)-6-methylphenyl]acetamide |
| terbuthylazine | 2-(tert-butylamino)-4-chloro-6-(ethylamino)-s-triazine |
| terbutol | 2,6-di-tert-butyl-p-tolyl methylcarbamate |
| terbutryn | 2-(tert-butylamino)-4-(ethylamino)-6-methylthio)-s-triazine |
| tetrafluron | N,N—dimethyl-N'—[3-(1,1,2,2-tetrafluoroethoxy)phenyl]urea |
| thiobencarb | S—[(4-chlorophenyl)methyl] diethylcarbamothioate |
| triallate | S—(2,3,3-trichloroallyl)diisopropyl- |

-continued

| Common Name | Chemical Name |
|---|---|
| | thiocarbamate |
| trifluralin | α,α,α-trifluoro-2,6-dinitro-N,N—dipropyl-p-toluidine |
| trimeturon | 1-(p-chlorophenyl)-2,3,3-trimethylpseudourea |
| 2,3,6-TBA | 2,3,6-trichlorobenzoic acid and agriculturally suitable salts and esters thereof |
| 2,4-D | (2,4-dichlorophenoxy)acetic acid and agriculturally suitable salts and esters thereof |
| 2,4-DB | 4-(2,4-dichlorophenoxy)butyric acid and agriculturally suitable salts and esters thereof |
| 2,4-DEP | tris[2-(2,4-dichlorophenoxy)-ethyl] phosphite |
| methabenzthiazuron | 1,3-dimethyl-3-(2-benzothiazolyl)-urea |
| chlortoluran | N'—(3-chloro-4-methylphenyl)-N'N—dimethylurea |
| isoproturan | N—(4-isopropylphenyl)-N'N'—di-dimethylurea |
| metoxuran | N'—(3-chloro-4-methoxyphenyl)-N,N—dimethylurea |

When an added herbicide is water-soluble, the pH of the resulting composition may need to be adjusted to lie within the range of 6 to 9.

The following examples illustrate methods for preparing the complexes of sulfonylurea salts of Formula I with ureas of Formula II wherein $R_1$ is H or $CH_3$ and $R_{12}$ and $R_{13}$ are H.

EXAMPLE 1

Thirty grams of 2-[[(4-methoxy-6-methyl-1,3,5-triazin-2-yl)aminocarbonyl]aminosulfonyl]benzoic acid, methyl ester of 98.9% purity (0.0778 mole) were added to 100 g water containing 3.1 g (0.0778 mole) sodium hydroxide with vigorous stirring. A clear solution of the sodium salt of the sulfonylurea was formed, pH 7.61. To the solution then was added a solution of 18.7 g (0.31 mole) urea in 50 g water. The initially clear mixture clouded rapidly in less than one minute and precipitation of fine crystals occurred. After 30 minutes, the slurry was filtered and the cake was washed with cold methanol and dried. The water-soluble product weighed 34 g and was analyzed as a 1:1 molar complex of the sodium salt of the sulfonylurea and urea.

EXAMPLE 2

One gram of any one of the preformed sodium salts of the following sulfonylureas:
A. 5-[[(4,6-dimethoxypyrimidin-2-yl)aminocarbonyl]aminosulfonyl]-1-methyl-1H-pyrazole-4-carboxylic acid, ethyl ester
B. N-[[4-ethoxy-6-(methylamino)-1,3,5-triazin-2-yl]aminocarbonyl]-3,4-dihydro-3-methyl-1-oxo-1H-2-benzopyran-8-sulfonamide
C. N-[[4-(2,2,2-trifluoroethoxy)-6-methoxy-1,3,5-triazin-2-yl]aminocarbonyl]-2-ethoxybenzenesulfonamide
D. N-[(4-methoxy-6-methyl-1,3,5-triazin-2-yl)aminocarbonyl]-2-(2-chloroethoxy)benzenesulfonamide,
was dissolved in 15 ml of methanol and then the solution was mixed with 10 ml of a methanolic solution of urea containing two equivalents of urea per equivalent of sulfonylurea salt. A precipitate of the 1:1 molar complex rapidly formed.

EXAMPLE 3

Thirty grams (0.0778 mole) of the sulfonylurea of Example 1 was neutralized with 4.36 g (0.0778 mole) potassium hydroxide and the salt was mixed with 18.7 g (0.31 mole) urea as described in Example 1. Precipitation of a course granular solid began several minutes later and was complete in 15 minutes. The product was isolated and identified as a 1:1 molar complex of the potassium salt of the sulfonylurea and urea; yield 26.5 g.

EXAMPLE 4

Preformed lithium salt of the sulfonylurea of Example 1 was used in the following experiments to show the effect of varying the proportion of urea-to-sulfonylurea salt upon the composition of the complex formed:
A. 21.5 g (0.05 mole) lithium salt of sulfonylurea in 60 g methanol was mixed with 3.03 g (0.05 mole) urea. A complex rapidly formed and was isolated and dried; 12.6 g.
B. Experiment A was repeated with 6.06 g (0.10 mole) urea; 13.9 g complex was obtained.
C. Experiment A was repeated with 12.12 g (0.20 mole) urea; 18.9 g complex was obtained.

Analyses showed that all of the products which were formed by combining urea and the lithium salt of the sulfonylurea in proportions of 1:1 (A.), 2:1 (B.) and 4:1 (C.) had the same 1:1 molar composition.

In the following examples, 1:1 molar complexes of sulfonylurea salts and urea were prepared as described in Example 1:

| Ex. | Sulfonylurea (Neutralizing Agent) | Solvent |
|---|---|---|
| 5 | A (LiOH) | Water |
| 6 | B (NaOH) | Methanol |
| 7 | C (NaOH) | Methanol |
| 8 | D (KOH) | Methanol |

A=2-chloro-N-[(4-methoxy-6-methyl-1,3,5-triazin-2-yl)aminocarbonyl]benzenesulfonamide;
B=2-[[(4,6-dimethoxypyrimidin-2-yl)aminocarbonyl]aminosulfonylmethyl]benzoic acid, methyl ester;
C=3-[[(4-methoxy-6-methyl-1,3,5-triazin-2-yl)aminocarbonyl]aminosulfonyl]-2-thiophenecarboxylic acid, methyl ester;
D=2-[(4,6-dimethylpyrimidin-2-yl)aminocarbonyl]aminosulfonyl]benzoic acid, methyl ester.

EXAMPLE 9

To a dispersed mixture of 11.57 g (0.03 mole) of the sulfonylurea of Example 1 and 3.33 g (0.045 mole) of methylurea in 40 g ethyl alcohol was added 1.20 g (0.03 mole) of sodium hydroxide in 2 ml water. Upon stirring, a clear solution formed and shortly thereafter a fine solid rapidly precipitated. The slurry was cooled in ice water for 30 minutes and filtered. The cake was washed with ice-cold ethanol and dried to give 13.85 g of a product identified as a 1:1 molar complex of the lithium salt of the sulfonylurea and methylurea.

The following examples illustrate methods for preparing the complexes of sulfonylurea salts of Formula I with ureas of Formula II wherein at least one of $R_1$, $R_{12}$ and $R_{13}$ is other than H.

EXAMPLE 10

Thirteen grams (0.03 mole) of the lithium salt of the sulfonylurea of Example 1 was dispersed in 30 g acetone. The solubility of the salt had been previously determined as less than 5%. To the stirred suspension was added solid n-butylurea in portions. With each addition of n-butylurea, part of the sulfonylurea salt dissolved until, after about 4.4 g (0.0375 mole) had been added, a clear solution was obtained. This gave a solution which contained 27.4% of the sulfonylurea salt as a complex of n-butylurea. Preparation of a solution containing greater than 50% of the sulfonylurea salt was accomplished by evaporation of acetone.

EXAMPLE

Twenty-two and six-tenths grams (0.06 mole) of 2-chloro-N-[(4-methoxy-6-methyl-1,3,5-triazin-2-yl)aminocarbonyl]benzenesulfonamide of 95% purity and 9.75 g (0.075 mole) of n-pentylurea were slurried in 60 g methyl isobutyl ketone. Both solids had low solubility in the solvent. With rapid stirring, 2.56 g (0.061 mole) solid lithium hydroxide hydrate were added. The solids rapidly dissolved as the salt was formed and complexed with the urea compound. The sulfonylurea salt concentration in methyl isobutyl ketone was 26.5%. Without n-pentylurea present, the concentration of the salt would have been less than 5%.

In the following examples, complexes of sulfonylurea salts and ureas are prepared as described in Example 10.

| Ex. | Sulfonylurea (Neutralizing Agent) | Urea | Solvent |
|---|---|---|---|
| 12 | A (KOH) | 1,3-Dimethylurea | Methanol |
| 13 | B (NaOH) | 1,1-Diethylurea | Isopropanol |
| 14 | C (LiOH) | n-Dodecylurea | γ-Butyrolactone |
| 15 | D (LiOH) | Cyclohexylurea | N—Methylpyrrolidine |
| 16 | E (LiOH) | $(CH_2)_5 N\text{—}\overset{O}{\overset{\|}{C}}\text{—}NH_2$ | Cyclohexanone |
| 17 | F (LiOH) | 2-Butenylurea | Ethyl Lactate |

A=2-[[(4-methoxy-6-methyl-1,3,5-triazin-2-yl)aminocarbonyl]aminosulfonyl]benzoic acid, methyl ester;
B=2-[[(4,6-dimethoxypyrimidin-2-yl)aminocarbonyl]aminosulfonylmethyl]benzoic acid, methyl ester;
C=3-[[(4-methoxy-6-methyl-1,3,5-triazin-2-yl)aminocarbonyl]aminosulfonyl]-2-thiophenecarboxylic acid, methyl ester;
D=N-[(4,6-dimethylpyrimidin-2-yl)aminocarbonyl;]-2-hydroxybenzenesulfonamide, ethanesulfonate;
E=2-[[(4,6-dimethylpyrimidin-2-yl)aminocarbonyl]aminosulfonyl]benzoic acid, methyl ester;
F=2-chloro-N-[(4-methoxy-6-methyl-1,3,5-triazin-2-yl)aminocarbonyl]benzenesulfonamide.

EXAMPLE 18

Four grams (0.01 equivalent) of the calcium salt of 2-[[(4-methoxy-6-methyl-1,3,5-triazin-2-yl)aminocarbonyl]aminosulfonyl]benzoic acid, methyl ester was dispersed in 30 ml acetone and 1.65 g (0.015 mole) n-butylurea was added. A clear solution formed but precipitation began shortly afterward. The precipitate was filtered, washed with acetone and dried. A yield of 4.6 g product was obtained. Analyses showed that the product was a complex of two moles n-butylurea per mole of the calcium salt of the sulfonylurea.

EXAMPLE 19

Four and three-tenths grams (0.01 mole) of the sodium salt of 2-[[(4-methoxy-6-methyl-1,3,5-triazin-2-yl)aminocarbonyl]aminosulfonyl]benzoic acid, methyl ester and 1.29 g (0.015 mole) 2-imidazolidone, a cyclic urea compound, were dissolved in a mixture of 25 g methanol-5 g water. A precipitate formed over a period of several hours, was filtered, washed with methanol-water and dried. Total product weighed 4.4 g. Analyses showed that the product was a 1:1 molar complex of the urea and sulfonylurea salt.

The following examples describe herbicidal formulations prepared from complexes of sulfonylurea salts with ureas:

EXAMPLE 20

Solution

Twelve and one-half grams of a 93% purity lithium salt of the sulfonylurea of Example 1 (0.03 mole active material) and 4.4 g (0.0375 g) n-butylurea were dissolved in 40 g γ-butyrolactone to give a 20% solution of active sulfonylurea. On accelerated aging for 3 weeks at 45° C., the relative decomposition of active component was 3.15%. The water content was measured as 0.75%. A similar composition with this level of water containing no n-butylurea showed 18% relative decomposition.

This example illustrates the improved hydrolytic stability of a sulfonylurea when its salt is complexed with a substituted urea.

In the following examples, other solutions of sulfonylurea salts complexed with n-octylurea are shown to have improved stability.

| Ex. | Sulfonylurea Salt | Solvent (% $H_2O$) | % Rel. Decomp. w Urea | % Rel. Decomp. w/o Urea |
|---|---|---|---|---|
| 21 | A | Acetonitrile (1.25) | 2.0 | 12.0 |
| 22 | B | Methyl Isobutyl Ketone (0.65) | 1.5 | 10.5 |

A=3-[[(4-methoxy-6-methyl-1,3,5-triazin-2-yl)aminocarbonyl]aminosulfonyl]-2-thiophenecarboxylic acid, methyl ester;
B=2-[[(4,6-dimethylpyrimidin-2-yl)aminocarbonyl]aminosulfonyl]benzoic acid, methyl ester.

EXAMPLE 23

| Wettable Powder | |
|---|---|
| Complex of Example 1 | 40.0% |
| dioctyl sodium sulfosuccinate | 1.5% |
| sodium ligninsulfonate | 3.0% |
| low viscosity methyl cellulose | 1.5% |
| attapulgite | 54.0% |

The ingredients are thoroughly blended, passed through an air mill to produce an average particle size under 15 microns, reblended, and sifted through a U.S.S. No. 50 sieve (0.3 mm opening) before packaging.

EXAMPLE 24

| Oil Suspension | |
|---|---|
| Complex of Example 5 | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 25

| Granules | |
|---|---|
| Wettable powder of Example 23 | 15% |
| gypsum | 69% |
| potassium sulfate | 16% |

The ingredients are blended in a rotating mixer and water is sprayed onto the blend to accomplish granulation. When most of the material has reached the desired range of 1.0 to 0.42 mm (U.S.S. #18 to 40 sieves), the granules are moved, dried, and screened. Oversize material is crushed to produce additional material in the desired range.

EXAMPLE 26

| Dust | |
|---|---|
| complex of Example 7 | 10% |
| attapulgite | 10% |
| talc | 80% |

The active ingredient is blended with attapulgite and then passed through a hammer mill to produce particles substantially all below 200 microns. The ground concentrate is then blended with powdered talc until homogeneous.

EXAMPLE 27

| Aqueous Suspension | |
|---|---|
| complex of Example 9 | 21.3% |
| sodium ligninsulfonate | 1.11% |
| sodium acetate | 18.71% |
| polysaccharide thickener | 0.05% |
| water and impurities | balance |

With stirring, the sodium ligninsulfonate and complex is added to the water. To this mixture is added the sodium acetate in portions over a period of 30 minutes. The resulting composition is ground in a sand mill to produce particles essentially under five microns in size. The polysaccharide thickener is added several minutes before completion of the milling operation. The suspension is passed through a 50 mesh screen to remove milling material.

Utility

Test results indicate that the compounds of the present invention are highly active preemergent or postemergent herbicides or plant growth regulants. Many of them have utility for broad-spectrum pre- and or post-emergence weed control in areas where complete control of all vegetation is desired, such as around fuel storage tanks, ammunition depots, industrial storage areas, parking lots, drive-in theaters, around billboards, highway and railroad structures. Some of the compounds have utility for selective weed control in crops such as rice, wheat, and barley. Alternatively, the subject compounds are useful to modify plant growth.

The rates of application for the compounds of the invention are determined by a number of factors, including their use as plant growth modifiers.or as herbicides, the crop species involved, the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for plant growth modification or for situations where only short-term persistence is required.

The compounds of the invention may be used in combination with any other commercial herbicide; examples of which are those of the triazine, triazole, uracil, urea, amide, diphenylether, carbamate and bipyridylium types. The compounds may also be used in combination with mefluidide.

The herbicidal properties of the subject compounds were discovered in a number of greenhouse tests. The test procedures and results follow.

TEST A

Seeds of crabgrass (Digitaria sp.), barnyardgrass (*Echinochloa crusgalli*), wild oats (*Avena fatua*), sicklepod (*Cassia obtusifolia*), morningglory (Ipomoea spp.), cocklebur (*Xanthium pensylvanicum*), sorghum, corn, soybean, sugar beet, cotton, rice, wheat and purple nutsedge (*Cyperus rotundus*) tubers were planted and treated pre-emergence with the test chemicals dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
B=burn;
D=defoliation;
E=emergence inhibition;
G=growth retardation;
H=formative effect;
U=unusual pigmentation;
X=axillary stimulation;
S=albinism; and
6Y=abscised buds or flowers.

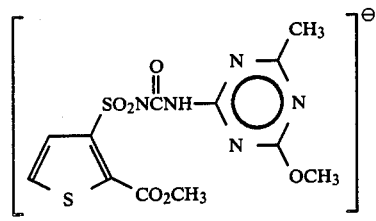 Complex 1
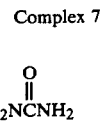 Na⊕ · H₂NCNH₂ (with O above C)

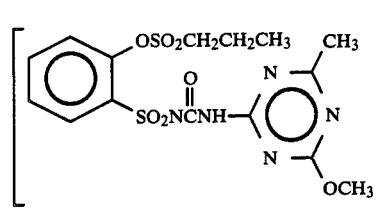 Complex 2
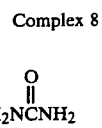 Na⊕ · H₂NCNH₂

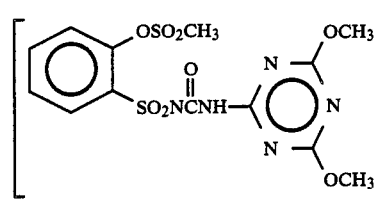 Complex 3
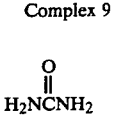 Na⊕ · H₂NCNH₂

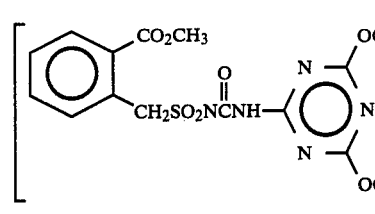 Complex 4
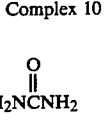 Na⊕ · H₂NCNH₂

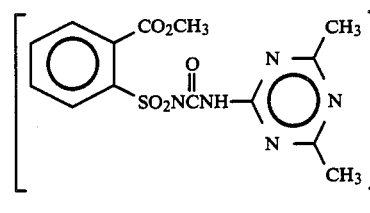 Complex 5
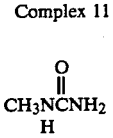 Na⊕ · H₂NCNH₂

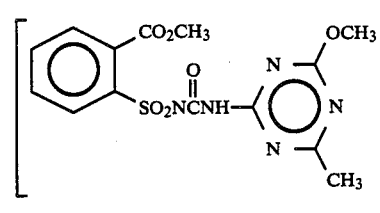 Complex 6
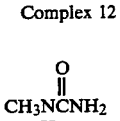 Na⊕ · H₂NCNH₂

-continued

 Complex 7
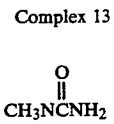 K⊕ · H₂NCNH₂

Complex 8 — Li⊕ · H₂NCNH₂

Complex 9 — Na⊕ · H₂NCNH₂

Complex 10 — Li⊕ · H₂NCNH₂

Complex 11 — Na⊕ · CH₃NCNH₂ (H)

Complex 12 — Li⊕ · CH₃NCNH₂ (H)

Complex 13 — Na⊕ · CH₃NCNH₂ (H)

TABLE A

| Rate kg/ha | Complex 1 .05 | Complex 2 .05 | Complex 3 .05 | Complex 4 .05 | Complex 5 .05 | Complex 6 .05 | Complex 7 .05 |
|---|---|---|---|---|---|---|---|
| POSTEMERGENCE | | | | | | | |
| Morningglory | 9C | 10C | 10C | 10C | 10C | 10C | 10C |
| Cocklebur | 10C | 10C | 10C | 8H | 10C | 10C | 9C |
| Sicklepod | 2C,5G | 5C,9G | 9C | 4C,9G | 10C | 10C | 9C |
| Nutsedge | 5G | 0 | 9C | 5C,9G | 6C,9G | 4C,9G | 5C,8G |

TABLE A-continued

| | | | | | | | |
|---|---|---|---|---|---|---|---|
| Crabgrass | 2C,8G | 2H | 4C,8G | 5G | 6C,9G | 9C | 6C,9G |
| Barnyardgrass | 3C,9H | 1H | 9C | 3H | 9C | 5C,9G | 6C,9G |
| Wild Oats | 2C | 0 | 3C,9G | 0 | 9C | 4C,8G | 2C,8G |
| Wheat | 2G | 0 | 3G | 0 | 9C | 4G | 4G |
| Corn | 8H | 0 | 2C,9G | 5H | 9C | 4U,9G | 3U,9G |
| Soybean | 4H | 2C,5H | 9C | 4C,9G | 9C | 9C | 9C |
| Rice | 5C,9G | 2G | 6C,9G | 2G | 9C | 9C | 9C |
| Sorghum | 2U,9G | 2C,4G | 9C | 6G | 9C | 5C,9G | 5C,9G |
| Sugar beet | 9C | 9C | 9C | 2C,7G | 9C | 9C | 9C |
| Cotton | 9C | 9C | 9C | 9C | 9C | 10C | 10C |
| PREEMERGENCE | | | | | | | |
| Morningglory | 9C | 9G | 9G | 9C | 9G | 9G | 9G |
| Cocklebur | 8H | 9H | 8H | 9H | 9H | 9H | 9H |
| Sicklepod | 8G | 5C,9G | 9G | 9G | 9G | 9G | 5C,9G |
| Nutsedge | 0 | 0 | 10E | 7E | 10E | 8G | 8G |
| Crabgrass | 3G | 2G | 3C,9G | 5G | 9C | 5C,9G | 2C,8G |
| Barnyardgrass | 3C,7H | 0 | 5C,9H | 5C,8G | 5C,9H | 4C,8H | 3C,9H |
| Wild Oats | 0 | 0 | 3C,8G | 3G | 9C | 4C,8G | 2C,8G |
| Wheat | 2G | 0 | 2G | 3G | 10H | 6G | 5G |
| Corn | 8G | 2C,5G | 3C,9G | 8G | 5C,9H | 3U,9H | 2U,9H |
| Soybean | 5G | 2C,6G | 9H | 3C,7H | 9H | 9H | 9H |
| Rice | 3C,8G | 0 | 5C,9H | 3G | 10E | 10E | 10E |
| Sorghum | 3C,9G | 5G | 5C,9H | 3C,8H | 5C,9H | 5C,9H | 5C,9H |
| Sugar beet | 5C,9G | 5C,9G | 9C | 9G | 6C,9G | 9C | 9C |
| Cotton | 9G | 9G | 10C | 9G | 2C,9G | 9C | 9C |

| | Complex 8 | Complex 9 | Complex 10 | Complex 11 | Complex 12 | Complex 13 |
|---|---|---|---|---|---|---|
| Rate kg/ha | .05 | .05 | .05 | .05 | .05 | .05 |
| POSTEMERGENCE | | | | | | |
| Morningglory | 10C | 10C | 9C | 9C | 9C | 9C |
| Cocklebur | 10C | 10C | 9C | 10C | 9C | 9C |
| Sicklepod | 9C | 9C | 9C | 9C | 9C | 9C |
| Nutsedge | 2C,8G | 3C,5G | 4G | 5G | 4G | 2C,8G |
| Crabgrass | 5C,9G | 4C,8G | 2C,7G | 4C,8G | 3C,8G | 4C,8G |
| Barnyardgrass | 5C,9H | 9C | 9C | 9C | 9C | 9C |
| Wild Oats | 2C,8G | 3G | 3G | 2G | 1C | 2C,8G |
| Wheat | 3G | 4G | 3G | 2G | 2G | 4G |
| Corn | 10C | 9G | 10C | 2U,9G | 4C,9G | 2U,9G |
| Soybean | 9C | 9C | 9C | 9C | 9C | 9C |
| Rice | 9C | 5C,9G | 6C,9G | 5C,9G | 5C,9G | 9C |
| Sorghum | 5C,9G | 3C,9H | 2C,9H | 4C,9H | 3C,9H | 3C,9G |
| Sugar beet | 9C | 9C | 9C | 9C | 9C | 9C |
| Cotton | 10C | 9C | 9C | 9C | 9C | 9C |
| PREEMERGENCE | | | | | | |
| Morningglory | 9C | 9G | 9C | 9G | 9C | 9G |
| Cocklebur | 9H | 9H | 9H | 9H | 8H | 9H |
| Sicklepod | 9G | 2C,9G | 9G | 3C,9G | 9G | 9G |
| Nutsedge | 2C,8G | 0 | 3G | 3G | 3G | 6G |
| Crabgrass | 3C,8G | 3C,7G | 6G | 8G | 8G | 2C,8G |
| Barnyardgrass | 3C,9H | 4C,9H | 4C,9H | 3C,9H | 3C,9H | 3C,9H |
| Wild Oats | 3C,7G | 3G | 2G | 3G | 2G | 2C,8G |
| Wheat | 5G | 2G | 2G | 3G | 2G | 1C,3G |
| Corn | 3U,9H | 3C,9H | 9G | 9G | 9G | 3C,9H |
| Soybean | 9H | 9H | 9H | 9H | 9H | 9H |
| Rice | 10E | 3C,9H | 5C,9H | 5C,9H | 5C,9H | 10E |
| Sorghum | 6C,9H | 5C,9H | 4C,9H | 5C,9H | 4C,9H | 6C,9H |
| Sugar beet | 9C | 9C | 9C | 9C | 9C | 9C |
| Cotton | 9C | 9G | 9G | 9C | 9G | 9C |

What is claimed is:

1. A complex selected from:

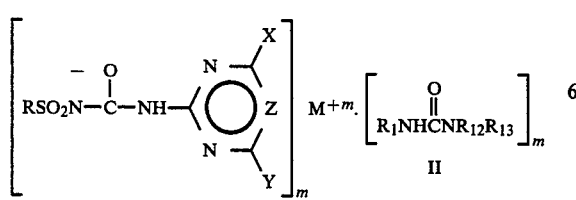

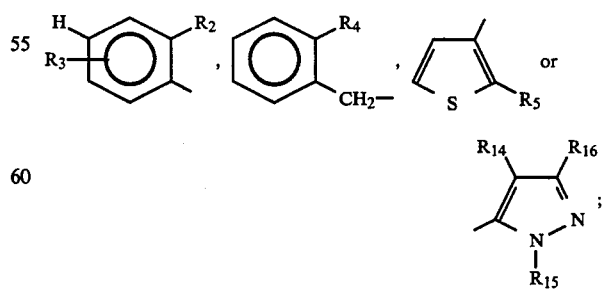

wherein
R is $R_1$ is H or $CH_3$;
$R_2$ is F, Cl, Br, $C_1$-$C_4$ alkyl optionally substituted with 1-3 atoms of F or Cl, $SO_2NR_6R_7$, $S(O)_nR_8$, $SO_2NCH_3(OCH_3)$, $CO_2R_9$, $OSO_2R_{10}$, $OR_{11}$, $NO_2$, $C_2-C_4$ alkenyl, $CONR_6R_7$, phenyl,

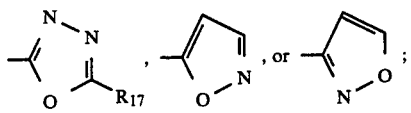

$R_3$ is H, F, Cl, Br, $CH_3$, $OCH_3$ or $CF_3$;
$R_4$ is Cl, $NO_2$, $CO_2R_{10}$;
$R_5$ is Cl, Br, $SO_2NR_6R_7$, $S(O)_nR_{10}$, $CO_2R_{10}$, $C_1-C_3$ alkyl, $NO_2$, $CON(CH_3)_2$ or $SO_2N(OCH_3)CH_3$;
$R_6$ is H or $C_1-C_3$ alkyl;
$R_7$ is H or $C_1-C_2$ alkyl;
$R_8$ is $C_1-C_3$ alkyl or $C_1-C_3$ alkyl substituted with 1–5 atoms of F, Cl or Br;
$R_9$ is $C_1-C_4$ alkyl, $CH_2CH_2OCH_3$, $CH_2CH_2Cl$ or $CH_2CH=CH_2$;
$R_{10}$ is $C_1-C_3$ alkyl;
$R_{11}$ is $C_1-C_4$ alkyl, $C_1-C_3$ alkyl substituted with 1–5 atoms of F, Cl or Br, $CH_2CH=CH_2$ or $CH_2C\equiv CH$;
$R_{12}$ is H, $C_1-C_{12}$ alkyl, $C_3-C_6$ cycloalkyl or $C_3-C_6$ alkenyl;
$R_{13}$ is H, $CH_3$ or $CH_2CH_3$ or $R_{12}$ and $R_{13}$ may be taken together to be $-(CH_2)_4-$ or $-(CH_2)_5-$ or $R_1$ and $R_{12}$ may be taken together to be $-(CH_2)_2-$;
$R_{14}$ is $C_1-C_3$ alkyl, F, Cl, Br, $NO_2$, $CO_2R_{10}$, $SO_2N(CH_3)_2$, $SO_2R_{12}$, or phenyl;
$R_{15}$ is H, $C_1-C_3$ alkyl, or $CH_2CH=CH_2$;
$R_{16}$ is H or $CH_3$;
$R_{17}$ is H or $CH_3$;
n is 0 or 2;
M is an alkali metal cation, magnesium or calcium;
Z is CH or N;
X is $CH_3$, $OCH_3$ or $OCHF_2$;
Y is $CH_3$, $OCH_3$, $CH(OCH_3)_2$, $OCHF_2$, $C_2H_5$, $OC_2H_5$, $OCH_2CF_3$ or $CH_2OCH_3$; and
m is 1 or 2.

2. A complex of claim 1 containing sulfonylurea salts of Formula I wherein R is

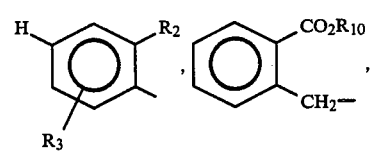

$R_2$ is Cl, $CH_3$, $SO_2N(CH_3)_2$, $S(O)_nR_8$, $CO_2R_9$, $OSO_2R_{10}$, $OR_{11}$, $NO_2$ or $CON(CH_3)_2$;
$R_3$ is H, Cl, $CH_3$, $OCH_3$ or $CF_3$;
$R_8$ is $C_1-C_3$ alkyl, $CF_3$, $CF_2H$ or $CF_2CF_2H$;
$R_9$ is $C_1-C_4$ alkyl; and
$R_{11}$ is $C_1-C_4$ alkyl, $CF_3$, $CF_2H$, $CF_2CF_2H$ or $CH_2CH_2Cl$.

3. A complex of claim 1 containing the urea of Formula II wherein $R_1$, $R_{12}$ and $R_{13}$ are H.

4. A complex of claim 2 where the sulfonylurea salt of Formula I is selected from the salts of:
2-[[(4-methoxy-6-methyl-1,3,5-triazin-2-yl)aminocarbonyl]aminosulfonyl]benzoic acid, methyl ester;
2-[(4,6-dimethylpyrimidin-2-yl)aminocarbonyl]aminosulfonyl]benzoic acid, methyl ester;
2-chloro-N-[(4-methoxy-6-methyl-1,3,5-triazin-2-yl)aminocarbonyl]benzenesulfonamide;
2-[[(4,6-dimethoxypyrimidin-2-yl)aminocarbonyl]aminosulfonylmethyl]benzoic acid, methyl ester;
5-[[(4,6-dimethoxypyrimidin-2-yl)aminocarbonyl]aminosulfonyl]-1-methyl-1H-pyrazole-4-carboxylic acid ethyl ester;
2-(2-Chloroethoxy)-N-[(4-methoxy-6-methyl-1,3,5-triazin-2yl)aminocarbonylbenzenesulfonamide; and
3-[[(4-methoxy-6-methyl-1,3,5-triazin-2-yl)aminocarbonyl]aminosulfonyl]-2-thiophenecarboxylic acid, methyl ester.

5. A complex of claim 4 containing the urea of Formula II where $R_1$, $R_{12}$ and $R_{13}$ are H.

6. A complex resulting from contacting

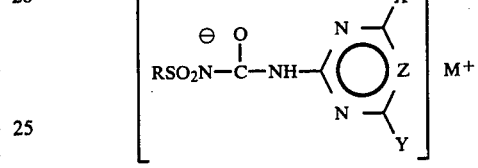

and

II
$$R_1NHCNR_{12}R_{13}$$
(with O above C)

at a molar ratio of about 1:1 in a solvent, wherein
R is

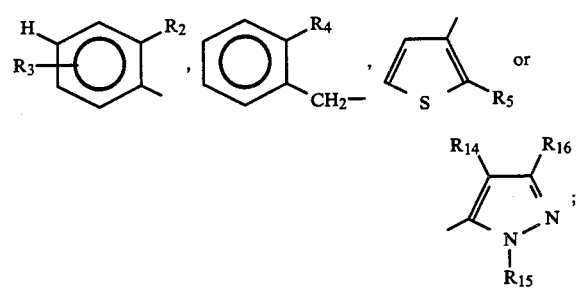

$R_1$ is H or $CH_3$;
$R_2$ is F, Cl, Br, $C_1-C_4$ alkyl optionally substituted with 1–3 atoms of F or Cl, $SO_2NR_6R_7$, $S(O)_nR_8$, $SO_2NCH_3(OCH_3)$, $CO_2R_9$, $OSO_2R_{10}$, $OR_{11}$, $NO_2$, $C_2-C_4$ alkenyl, $CONR_6R_7$, phenyl,

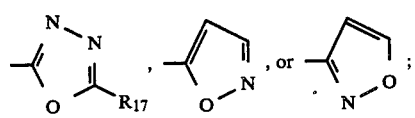

$R_3$ is H, F, Cl, Br, $CH_3$, $OCH_3$ or $CF_3$;
$R_4$ is Cl, $NO_2$, $CO_2R_{10}$;
$R_5$ is Cl, Br, $SO_2NR_6R_7$, $S(O)_nR_{10}$, $CO_2R_{10}$, $C_1-C_3$ alkyl, $NO_2$, $CON(CH_3)_2$ or $SO_2N(OCH_3)CH_3$;
$R_6$ is H or $C_1-C_3$ alkyl;
$R_7$ is H or $C_1-C_2$ alkyl;
$R_8$ is $C_1-C_3$ alkyl or $C_1-C_3$ alkyl substituted with 1–5 atoms of F, Cl or Br;

$R_9$ is $C_1$-$C_4$ alkyl, $CH_2CH_2OCH_3$, $CH_2CH_2Cl$ or $CH_2CH=CH_2$;

$R_{10}$ is $C_1$-$C_3$ alkyl;

$R_{11}$ is $C_1$-$C_4$ alkyl, $C_1$-$C_3$ alkyl substituted with 1-5 atoms of F, Cl or Br, $CH_2CH=CH_2$ or $CH_2C\equiv CH$;

$R_{12}$ is H, $C_1$-$C_{12}$ alkyl, $C_3$-$C_6$ cycloalkyl or $C_3$-$C_6$ alkenyl;

$R_{13}$ is H, $CH_3$ or $CH_2CH_3$ or $R_{12}$ and $R_{13}$ may be taken together to be $-(CH_2)_4-$ or $-(CH_2)_5-$ or $R_1$ and $R_{12}$ may be taken together to be $-(CH_2)_2-$;

$R_{14}$ is $C_1$-$C_3$ alkyl, F, Cl, Br, $NO_2$, $CO_2R_{10}$, $SO_2N(CH_3)_2$, $SO_2R_{12}$, or phenyl;

$R_{15}$ is H, $C_1$-$C_3$ alkyl, or $CH_2CH=CH_2$;

$R_{16}$ is H or $CH_3$;

$R_{17}$ is H or $CH_3$;

n is 0 or 2;

M is an alkali metal cation;

Z is CH or N;

X is $CH_3$, $OCH_3$ or $OCHF_2$ and

Y is $CH_3$, $OCH_3$, $CH(OCH_3)_2$, $OCHF_2$, $C_2H_5$, $OC_2H_5$, $OCH_2CF_3$ or $CH_2OCH_3$.

7. A complex of claim 6 prepared from sulfonylurea salts of Formula I
wherein
R is

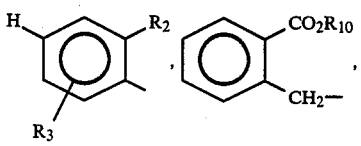

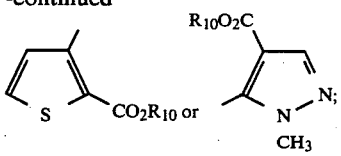

$R_2$ is Cl, $CH_3$, $SO_2N(CH_3)_2$, $S(O)_nR_8$, $CO_2R_9$, $OSO_2R_{10}$, $OR_{11}$, $NO_2$ or $CON(CH_3)_2$;

$R_3$ is H, Cl, $CH_3$, $OCH_3$ or $CF_3$;

$R_8$ is $C_1$-$C_3$ alkyl, $CF_3$, $CF_2H$ or $CF_2CF_2H$;

$R_9$ is $C_1$-$C_4$ alkyl; and $R_{11}$ is $C_1$-$C_4$ alkyl, $CF_3$, $CF_2H$, $CF_2CF_2H$ or $CH_2CH_2Cl$.

8. A complex of claim 6 prepared from ureas of Formula II
wherein
$R_1$ is H;
$R_{12}$ is $C_2$-$C_6$ alkyl; and
$R_{13}$ is H.

9. A complex of claim 6 where the sulfonylurea salt is selected from the salts of:

2-[[(4-methoxy-6-methyl-1,3,5-triazin-2-yl)aminocarbonyl]aminosulfonyl]benzoic acid, methyl ester;

2-[[(4,6-dimethylpyrimidin-2-yl)aminocarbonyl]aminosulfonyl]benzoic acid, methyl ester;

2-chloro-N-[(4-methoxy-6-methyl-1,3,5-triazin-2-yl)aminocarbonyl]benzenesulfonamide;

2-[[(4,6-dimethoxypyrimidin-2-yl)aminocarbonyl]aminosulfonylmethyl]benzoic acid, methyl ester;

5-[[(4,6-dimethoxypyrimidin-2-yl)aminocarbonyl]aminosulfonyl]-1-methyl-1H-pyrazole-4-carboxylic acid, ethyl ester;

2-(2-chloroethoxy)-N-[(4-methoxy-6-methyl-1,3,5-triazin-2-yl)aminocarbonyl]benzenesulfonamide; and 3-[[(4-methoxy-6-methyl-1,3,5-triazin-2yl)aminocarbonyl]aminosulfonyl]-2-thiophenecarboxylic acid, methyl ester.

* * * * *